United States Patent
Balda et al.

(10) Patent No.: US 8,983,583 B2
(45) Date of Patent: Mar. 17, 2015

(54) CARDIAC EVENT MONITORING SYSTEM

(75) Inventors: Daniel Balda, Ormond Beach, FL (US); Robert Michael Thomas, Melbourne, FL (US); Monte Marek, Palm Bay, FL (US); Tary Mann, Satellite Beach, FL (US); Anthony Balda, W. Melbourne, FL (US)

(73) Assignee: Medicomp, Inc., Melbourne, FL (US)

( * ) Notice: Subject to any disclaimer, the term of this patent is extended or adjusted under 35 U.S.C. 154(b) by 1207 days.

(21) Appl. No.: 11/550,759

(22) Filed: Oct. 18, 2006

(65) Prior Publication Data
US 2008/0097231 A1 Apr. 24, 2008

(51) Int. Cl.
| | |
|---|---|
| *A61B 5/04* | (2006.01) |
| *A61B 5/0408* | (2006.01) |
| *A61B 5/024* | (2006.01) |
| *A61B 5/0404* | (2006.01) |
| *A61B 5/0432* | (2006.01) |

(52) U.S. Cl.
CPC .......... *A61B 5/0408* (2013.01); *A61B 5/02438* (2013.01); *A61B 5/0404* (2013.01); *A61B 5/0432* (2013.01); *A61B 2560/0209* (2013.01); *A61B 2562/226* (2013.01)
USPC ....................................................... 600/509

(58) Field of Classification Search
USPC ....................................................... 600/509
See application file for complete search history.

(56) References Cited

U.S. PATENT DOCUMENTS

| | | | |
|---|---|---|---|
| 3,556,084 A * | 1/1971 | Budde | 600/479 |
| 4,583,553 A | 4/1986 | Shah et al. | |
| 5,027,824 A | 7/1991 | Dougherty et al. | |
| 5,285,783 A * | 2/1994 | Secker | 600/323 |
| 5,316,008 A * | 5/1994 | Suga et al. | 600/513 |
| 6,032,060 A * | 2/2000 | Carim et al. | 600/372 |
| 6,366,871 B1 * | 4/2002 | Geva | 702/188 |
| 6,783,492 B2 | 8/2004 | Dominguez et al. | |
| 7,222,054 B2 * | 5/2007 | Geva | 702/188 |
| 2004/0010201 A1 | 1/2004 | Korzinov et al. | |

FOREIGN PATENT DOCUMENTS

WO WO 85/05547 12/1985

OTHER PUBLICATIONS

Patient Instructions WristRecorder™ Plus, LifeWatch, (www.lifewatchinc.com), Feb. 2004, 8 pages.
Patient Instructions Micro ER, Life Watch, (www.lifewatchinc.com), prior to Oct. 18, 2006, 8 pages.
ReadMyHeart V2.0, DailyCare BioMedical Inc., Taiwan, (www.dcbiomed.com), 2005, 45 pages.

(Continued)

*Primary Examiner* — Niketa Patel
*Assistant Examiner* — William Levicky
(74) *Attorney, Agent, or Firm* — Mark R. Malek; William H. Harding; Widerman Malek, PL

(57) ABSTRACT

A cardiac event monitoring system includes a base unit including a base connector, a wearable electrode system, and a plug-in adapter. The wearable electrode system includes a cable, an electrode at one end of the cable, and a cable connector at the other end of the cable. The cable connector is configured to plug into the base connector. The plug-in adapter includes electrodes and an adapter connector that is configured to plug into the base connector.

25 Claims, 6 Drawing Sheets

(56) References Cited

OTHER PUBLICATIONS

HeartOne™, Pocketsize Transtelephonic ECG Event Recorder, HeartOne Aerotel Medical Systems, (http://www.aerotel.com/HeartOne.asp?id=65), prior to Oct. 18, 2006, 1 page.

Handheld ECG, ReadMyHeart, DailyCare BioMedical Inc., Taiwan, (www.dcbiomed.com), prior to Oct. 18, 2006, 2 pages.

CardioPAL™. . . Medicomp's Event Monitoring Solution, Medicomp, (www.medicompinc.com), (1998), 2 pages.

PCT International Search Report (Application No. PCT/US2007/081668) filed Oct. 17, 2007, mailed Apr. 7, 2008 (3 pages).

PCT Written Opinion (Application No. PCT/US2007/081668) filed Oct. 17, 2007, mailed Apr. 7, 2008 (7 pages).

* cited by examiner

CARDIAC EVENT MONITORING SYSTEM

TECHNICAL FIELD

This description relates to a cardiac event monitoring system.

BACKGROUND

Cardiac event monitoring is a procedure that is conducted on patients who report symptoms that may be cardiac in origin, and that occur infrequently, such as, for example, three times or less in one week. The term "event monitoring" is used because traditionally the test relied on the occurrence of symptoms, or "events." When symptoms occur, the patient activates an event monitor to record her electrocardiogram (ECG). The patient carries the event monitor during the testing period, which can last for several days or up to, for example, 30 days.

SUMMARY

In one general aspect, a cardiac event monitoring system includes a base unit including a base connector, a wearable electrode system, and a plug-in adapter. The wearable electrode system includes a cable, an electrode at one end of the cable, and a cable connector at the other end of the cable. The cable connector is configured to plug into the base connector. The plug-in adapter includes electrodes and an adapter connector that is configured to plug into the base connector.

Implementations can include one or more of the following features. For example, the plug-in adapter can include two electrodes. The electrodes of the plug-in adapter can be each sized to receive a finger. The electrode of the wearable electrode system can be configured to be attached to a patient's skin. The electrodes of the plug-in adapter and the wearable electrode system can detect electrical signals from a patient's heart when coupled to the patient's skin.

The base unit can include a controller. The controller can be configured to operate in an auto capture mode, in manual mode, or in finger electrode mode. The base unit can include a speaker for transmitting data recorded from the plug-in adapter or the wearable electrode system. The base unit can include memory for storing data recorded from the plug-in adapter or the wearable electrode system. The base unit can include a display, and/or one or more input devices.

In another general aspect, a cardiac event monitoring system includes a base unit and a plug-in adapter. The base unit includes a base connector configured to receive a cable connector of a wearable electrode system. The plug-in adapter includes electrodes and an adapter connector configured to plug into the base connector of the base unit.

Implementations can include one ore more of the following features. For example, the base unit can include a controller that is configured to operate in an auto capture mode.

Each of the electrodes can be sized to receive a finger. The electrodes of the plug-in adapter can detect electrical signals from a patient's heart when coupled to the patient's skin.

The base unit can include a speaker for transmitting data recorded from the plug-in adapter or the wearable electrode system. The base unit can include memory for storing data recorded from the plug-in adapter or the wearable electrode system.

In another general aspect, a method of monitoring cardiac events includes determining whether a wearable electrode system is connected to a base unit of a monitoring system, and if the wearable electrode system is connected to the base unit, operating the base unit to receive electrical signals from an electrode of the wearable electrode system. The method also includes determining whether a plug-in adapter is connected to the base unit if the wearable electrode system is not connected to the base unit, and operating the base unit to receive electrical signals from electrodes of the plug-in adapter if the plug-in adapter is connected to the base unit.

Implementations can include one or more of the following features. For example, the method can also include transmitting the electrical signals to a monitoring center if it is determined that the patient requested that the electrical signals be transmitted.

Operating the base unit to receive electrical signals from the electrode of the wearable electrode system can include monitoring the patient's electrical signals and recording the electrical signals if it is determined that the electrical signals are abnormal. Operating the base unit to receive electrical signals from the electrode of the plug-in adapter can include receiving an electrical signal from the electrode of the plug-in adapter when the patient puts a finger on at least one of the electrodes.

The method can include storing in memory electrical signals received from the plug-in adapter or the wearable electrode system for a predetermined time or until a patient transmits the electrical signals. The method can include displaying instructions to a patient on the base unit. The method can include receiving instructions from a patient from one or more input devices on the base unit.

In a further general aspect, a method of monitoring cardiac events includes providing a plug-in adapter that includes electrodes and an adapter connector that is configured to plug into a base connector of a base unit. The base connector is configured to receive a cable connector of a wearable electrode system that includes a cable, an electrode at one end of the cable, and the cable connector at the other end of the cable.

In another general aspect, a plug-in adapter includes a housing, two finger electrodes on one side of the housing, and an adapter connector on another side of the housing. The adapter connector is configured to plug into a connector of a base unit of a cardiac event monitor.

The cardiac event monitoring system provides a system that enables a patient to use a standard event monitor that uses wearable electrodes but also provides a patient with the option to use finger electrodes if the patient is uncomfortable with or does not want to use the wearable electrodes. The plug-in adapter is designed to be compatible with the base unit that is already designed to connect with the wearable electrode system. Therefore, the standard base unit does not need to be redesigned for use with the finger electrodes. It can be used for either the wearable electrodes or the finger electrodes, providing more options to the patient in a complete package.

Other features will be apparent from the description, the drawings, and the claims.

DESCRIPTION OF DRAWINGS

Like reference symbols in the various drawings indicate like elements.

DETAILED DESCRIPTION

Cardiac event monitoring is used to evaluate a patient who experiences transient, infrequent symptoms of various forms of heart disease. Symptoms such as shortness of breath, dizziness, and palpitations are some of the common patient complaints. These symptoms may be caused by disturbances in the electrical signals that control the heart muscle contractions. The disturbances can be random, spontaneous, or emotion- or stress-induced.

Figure 1:
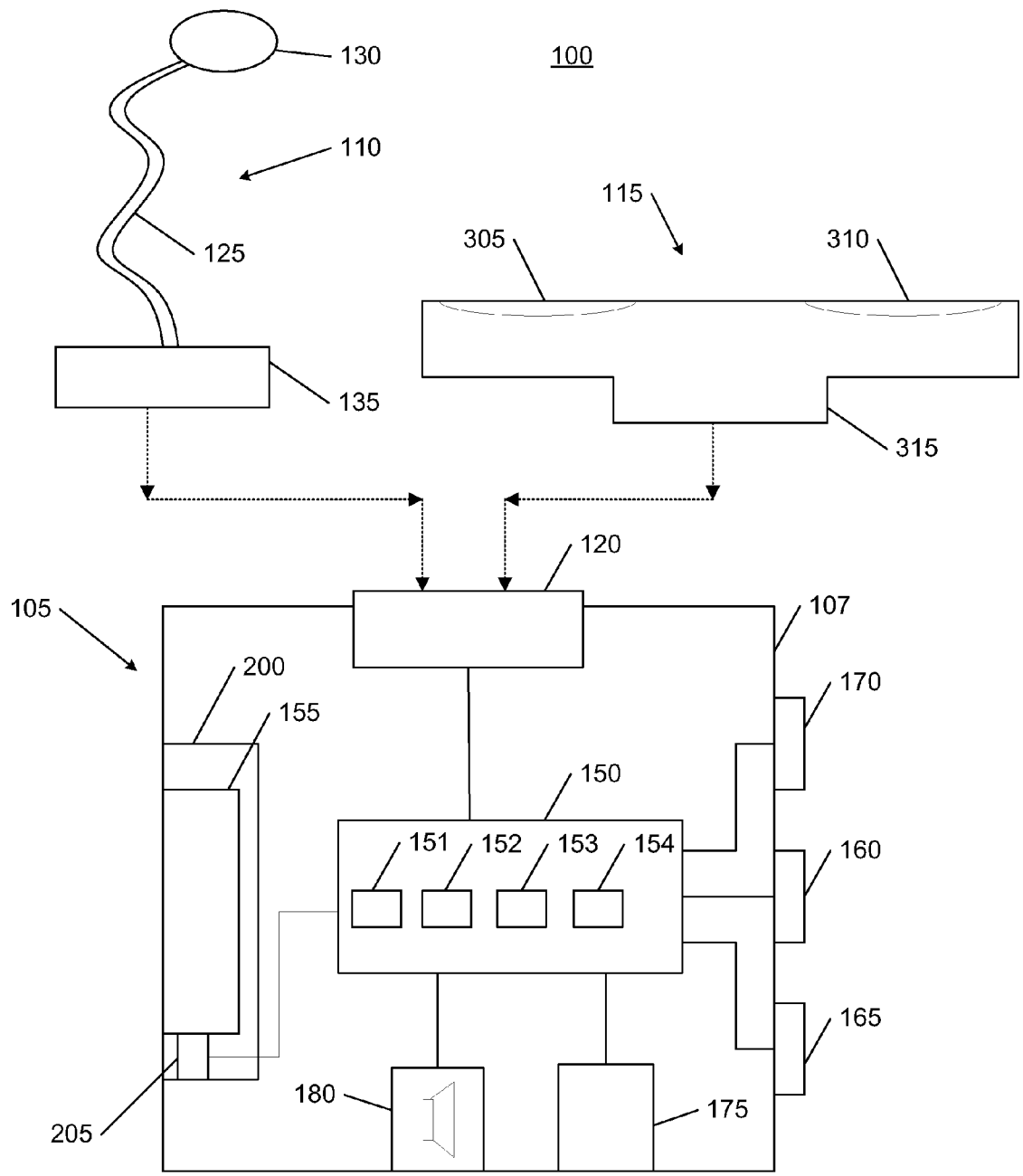
FIG. 1 is a block diagram of a cardiac event monitoring system.

Referring to FIG. 1, a cardiac event monitoring system 100 includes a base unit 105, a wearable electrode system 110, and a plug-in adapter 115. The base unit 105 includes a base connector 120 and a body 107 that houses the electrical components and includes a user interface, as discussed further below.

The wearable electrode system 110 includes a cable 125, at least two electrodes 130 at one end of the cable 125, and a cable connector 135 at the other end of the cable 125. The cable connector 135 is configured to plug into the base connector 120. Each electrode 130 is designed with a conducting member on a flat patch that contacts the patient's skin. In some cases, the flat patch of each electrode 130 is coated with a gel that improves electrical conduction between the patient's skin and the electrode surface. The patch can include an adhesive that sticks to the patient's skin. The electrodes 130 are usually placed along the patient's chest, at appropriate locations for producing the best ECG signal.

Figure 2A:
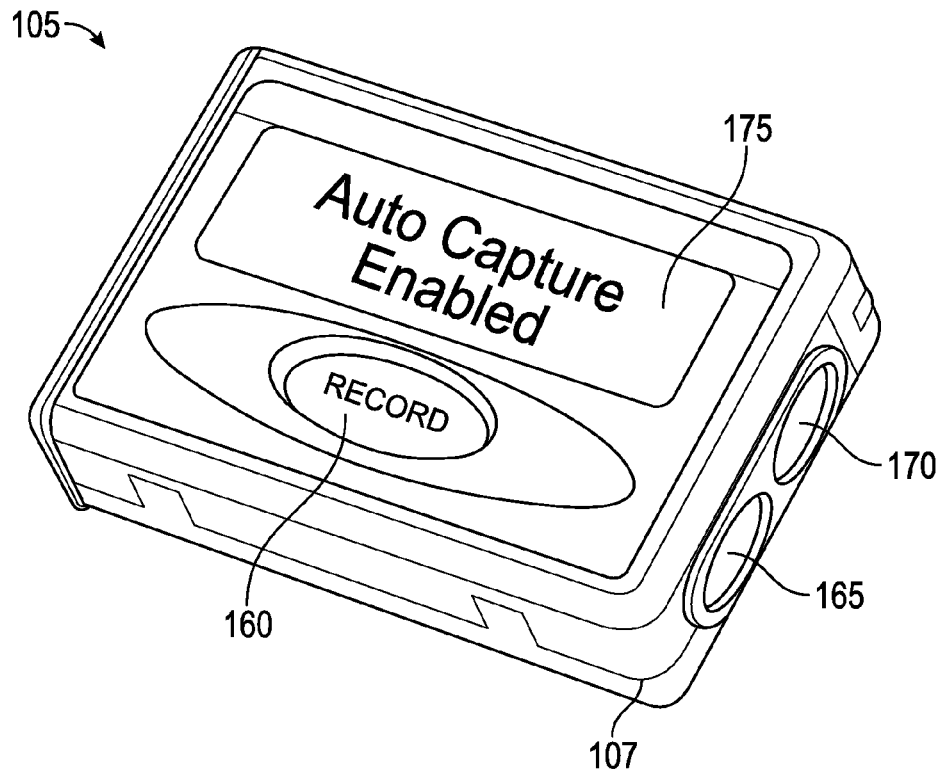
FIGS. 2A and 2B are perspective views of a base unit of the cardiac event monitoring system of FIG. 1.
Figure 2B:
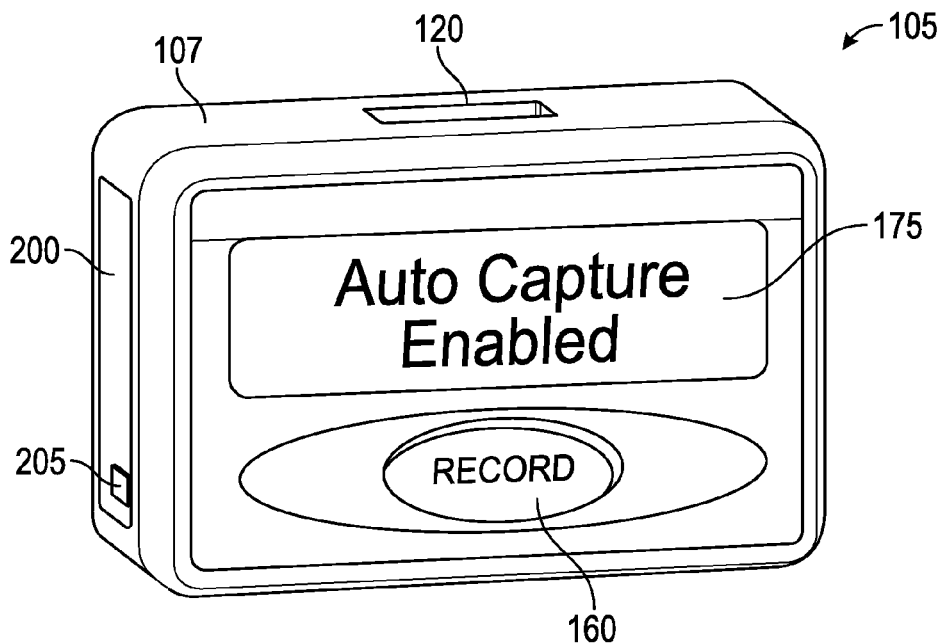

Referring also to FIGS. 2A and 2B, the base unit 105 is pager-sized, and is either handheld or patient-worn. The base unit 105 includes the body 107 that houses components that control operation of the system 100. Thus, the base unit 105 includes a controller 150 within the body 107, and various input and output devices coupled to the controller 150 through the body 107. The controller 150 receives power from a power source 155 that may be provided by batteries that are placed within a compartment 200 on a side of the body 107. The body 107 and the battery compartment 200 can be made of a suitable non-conductive lightweight material, such as a rigid plastic.

The controller 150 includes a processor 151, memory 152, a clock 153, and a counter 154 to process signals from the wearable electrode system 110 and/or the plug-in adapter 115, receive input from a patient or a service technician using the system 100, and transmit recorded data to a monitoring center, as provided by a health professional, a clinic, or a hospital. The input devices on the base unit 105 include a symptom record button 160, a yes/transmit button 165, and a no button 170. The yes/transmit button 165 can be used in one of two ways: it can be used as a response button to answer "yes" when queried by the controller 150, or it can be used to indicate to the controller 150 to transmit the ECG. The no button 170 can be used in one of two ways: it can be used as a response button to answer "no" when queried by the controller 150, it can be used to indicate to the controller 150 to cancel a transmission of an ECG.

The output devices on the base unit 105 include a display 175 such as a liquid crystal display (LCD) that provides an interface with the patient and/or a technician, and a speaker 180 for transmitting data regarding the recording.

The system 100 is designed to record, store, and transmit ambulatory ECG signals received from the wearable electrode system 110 or the plug-in adapter 115. The system 100 can be worn for days or weeks, as it is intended for use by patients who are experiencing symptoms that are transient and infrequent in nature. The base unit 105 can be worn outside the patient's clothing if there is any chance that moisture (for example, sweat) might come in contact with the base unit 105. The base unit 105 can be worn under outer wear, such as raincoats or jackets, for protection during wet or cold conditions.

A patient would normally operate the base unit 105 and the wearable electrode system 110 as a single unit to capture ECG data. However, some patients who want the features of the base unit 105 and the wearable electrode system 110 may also want the option of finger electrode capture, which is less irritating to the patient than using the wearable electrodes 130, which have to be placed on the patient's skin to obtain data. Thus, the plug-in adapter 115 is designed to couple with the base unit 105 when the wearable electrode system 110 is disconnected or detached from the base unit 105.

Referring to FIGS. 3A-3D, the plug-in adapter 115 includes a housing 300 having finger electrodes 305, 310 on one side of the housing 300 and an adapter connector 315 protruding from another side of the housing 300. The electrodes 305, 310 are positioned such that, when the adapter 115 is attached to the base unit 105, a patient may easily place the surface of a finger on each of the electrodes 305, 310 while holding the base unit 105. The fingers used by the patient may be any of the five terminating members of the patient's hand. The adapter connector 315 is configured to plug into the base connector 120 and the connections within the connector 315 are the same as those of the connector 135 of the wearable electrode system 110 to enable both the adapter 115 and the wearable electrode system 110 to be used with the base unit 105. The housing 300 is made of a lightweight non-conductive material such as a rigid plastic. The adapter 115 is generally sized to be smaller than the base unit 105 but large enough to accommodate the fingers at the electrodes 305, 310. The adapter 115 can be rectangular in shape, as shown in the drawings.

Figure 3A:
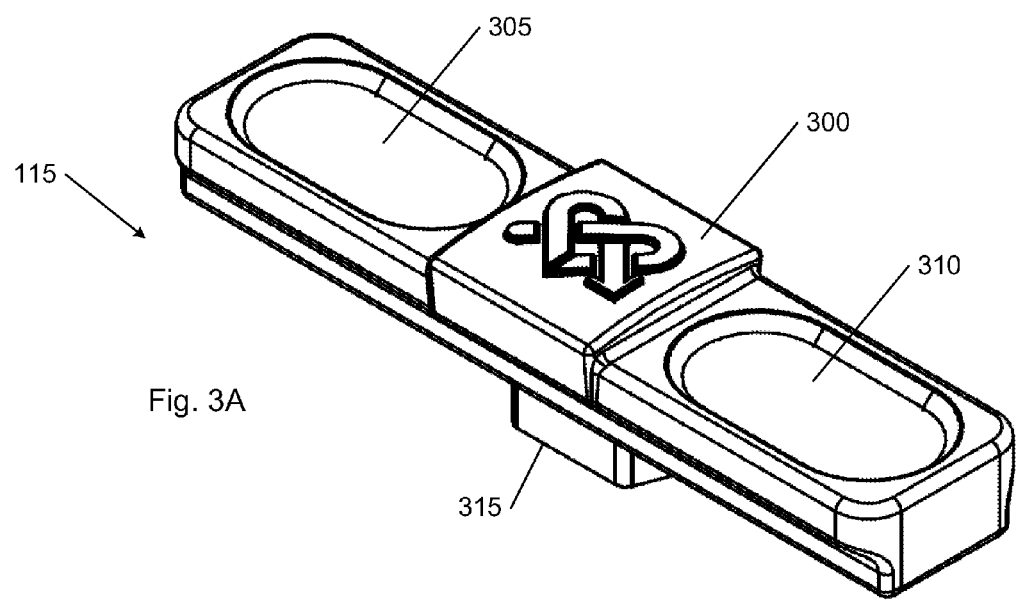
FIG. 3A is a perspective view of a plug-in adapter of the cardiac event monitoring system of FIG. 1.
Figure 3B:
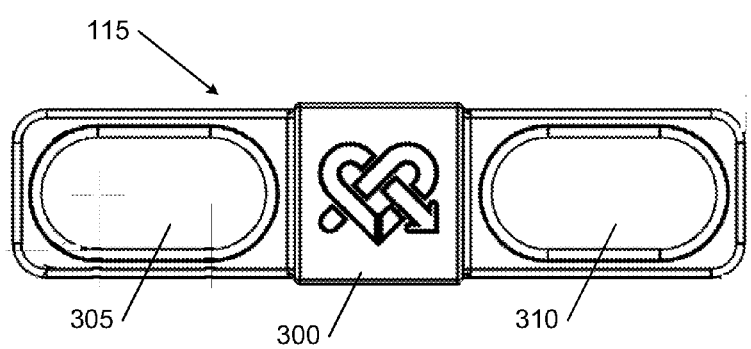
FIGS. 3B-3D are top, front, and side plan views of the plug-in adapter of FIG. 3A.
Figure 3C:
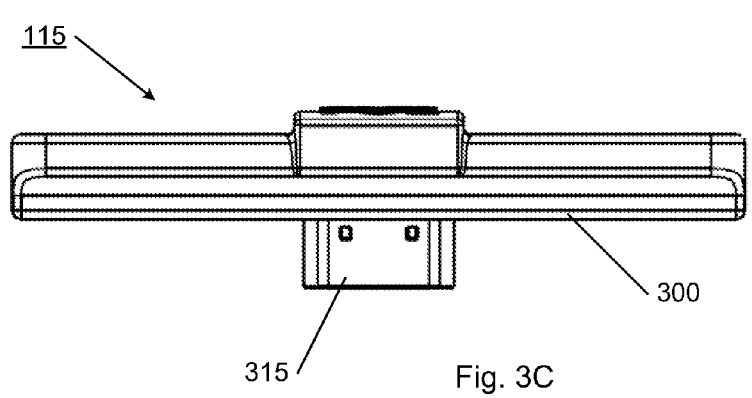
Figure 3D:
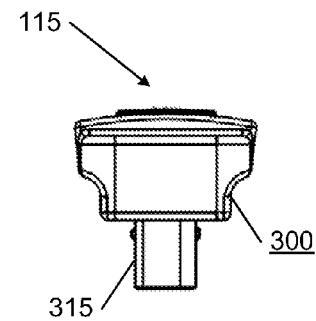
Figure 3E:
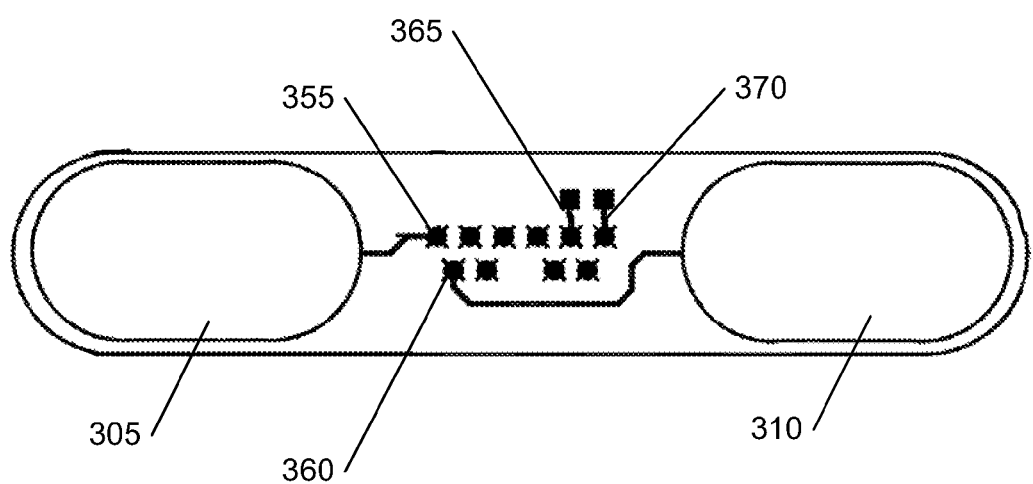
FIG. 3E is an electrical diagram of the plug-in adapter of FIG. 3A.

Referring also to FIG. 3E, the adapter 115 includes electrical connections 355, 360 from the electrodes 305, 310 to the adapter connector 315. The electrical connections 355, 360 connect to the controller 150 of the base unit 105 in the same fashion as the electrical connections within the wearable electrode system 110. Additionally, the adapter 115 includes a unique identifier that enables the base unit 105 to identify the adapter 115 when it is connected to the base unit 105. For example, the unique identifier can be formed from an internal resistance formed by resistors 365, 370 having a value unique to the adapter 115.

Figure 4:
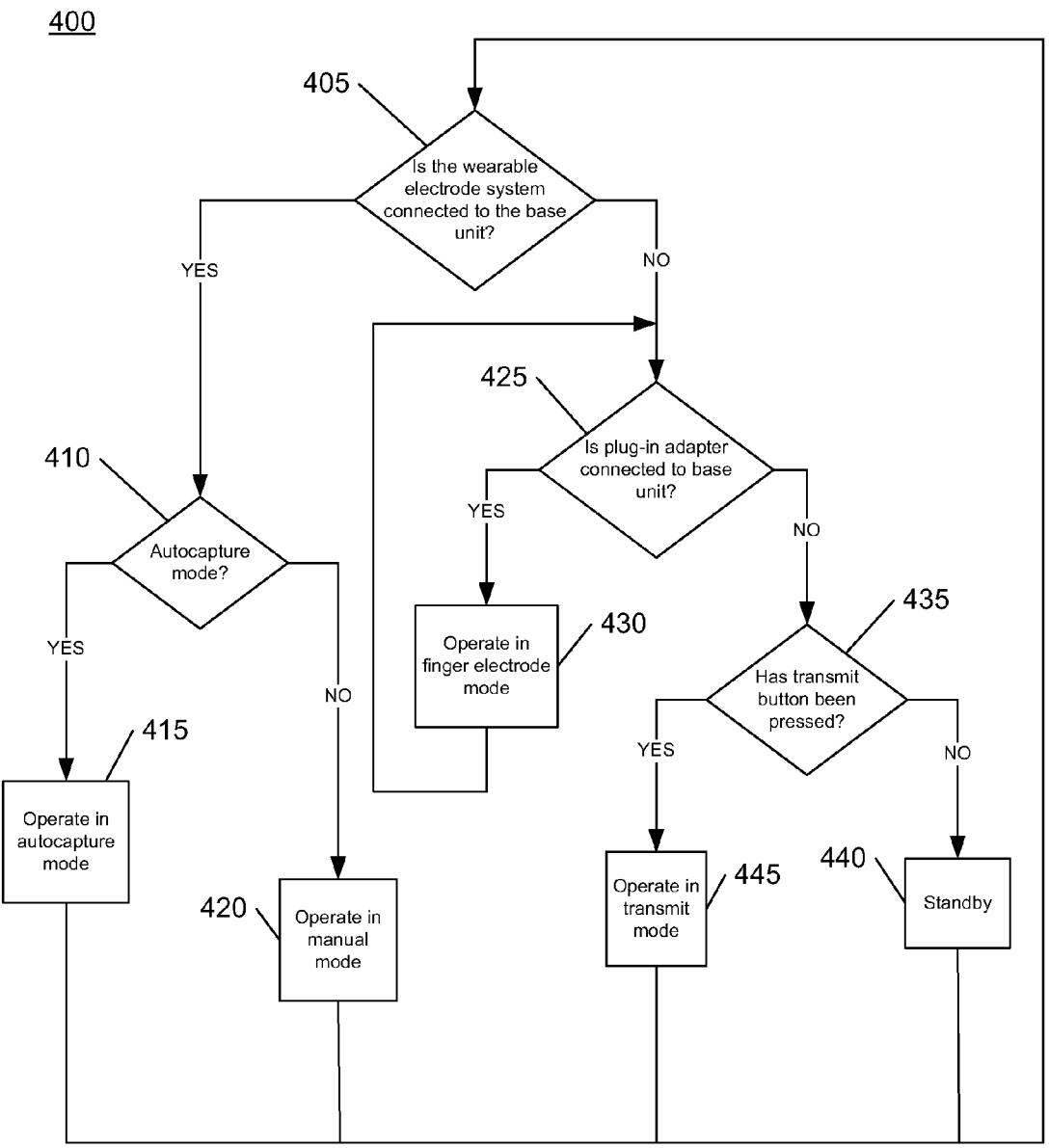
FIG. 4 is a flow chart of a procedure describing operation of the cardiac event monitoring system of FIG. 1.

Referring also to FIG. 4, a procedure 400 is performed by the cardiac event monitoring system 100 for monitoring cardiac events of a patient. In general the base unit 105 turns off after a period of inactivity to conserve energy of the power source 155. The base unit 105 can be set up so that the patient can turn on the base unit 105 by pressing any button on the base unit 105. Initially, the controller 150 determines whether the wearable electrode system 110 is connected to the base unit 105 (step 405). For example, the wearable electrode system 110 could be equipped with an internal resistance that is unique to the wearable electrode system 110, and the base unit 105 could detect the resistance when the wearable electrode system 110 is connected to the base unit 105. If the wearable electrode system 110 is connected to the base unit 105, then the controller 150 determines if the patient had set up the base unit 105 to operate in auto capture mode by, for example, selecting auto capture mode during a set up operation (step 410). If the patient had pre-selected the auto capture mode (step 410), then the controller 150 operates in the auto capture mode (step 415), a mode in which the controller 150 determines when to record the ECG, without the input from the patient.

During the auto capture mode (step 415), the patient carries the small, battery-powered system 100 on their person for the duration of the testing period. The electrodes 130 are attached to the patient's body, such as, for example, the patient's chest, using the associated adhesive patches, and the electrodes 130 detect the electrical signals from the patient's heart. The controller 150 continuously analyzes the signals from the electrodes 130 to detect an abnormality in the electrical signal of the heart. If the controller 150 detects an abnormality, the controller 150 records and stores the event data according to pre-defined protocols. Moreover, any memory 152 that is devoted to the auto capture mode can be dynamically managed and overwritten, as needed, for new activity. Moreover, the controller 150 can send a signal to the speaker 180 indicating to the patient that data has been recorded and that the patient should transmit that data to a monitoring center. The controller 150 operates in auto capture mode (step 415) until it receives an indication that the wearable electrode system 110 is disconnected from the base unit 105 (step 405) or unless the patient had set up the base unit 105 to operate in manual mode (step 410).

If the controller 150 determines that the wearable electrode system 110 is connected to the base unit 105 (step 405) and the patient set up the base unit 105 to operate in manual mode (step 410), then the controller 150 operates in a manual mode (step 420). As with the auto capture mode, the patient carries the battery-powered system 100 on their person for the duration of the testing period in the manual mode. The electrodes 130 are attached to the patient's body and the electrodes 130 detect the electrical signals from the patient's heart. When a symptom occurs, the patient triggers the controller 150 in the base unit 105 to record the ECG by pressing the symptom record button 160. The display 175 shows a countdown message while the recording takes place. The controller 150 operates in manual mode (step 420) until it receives an indication that the wearable electrode system 110 is disconnected from the base unit 105 (step 405) or unless the patient sets up the base unit 105 to operate in auto capture mode (step 410).

Figure 5:
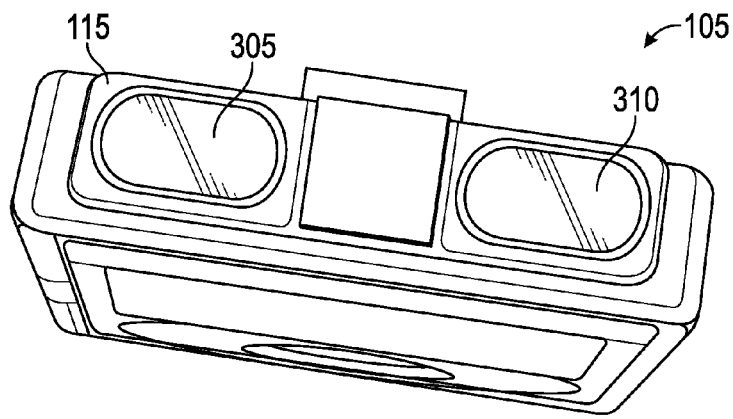
FIG. 5 is a perspective view showing the cardiac event monitoring system of FIG. 1 with the plug-in adapter of FIG. 3A connected to the base unit of FIGS. 2A and 2B.

If the controller 150 determines that the wearable electrode system 110 is not connected to the base unit 105 (step 405), then the controller 150 determines whether the plug-in adapter 115 is connected to the base unit 105 (step 425). For example, the plug-in adapter 115 could be equipped with the resistors 365, 370 having a resistance that is unique to the plug-in adapter, and the base unit 105 could detect the resistance when the plug-in adapter 115 is connected to the base unit 105. If the plug-in adapter 115 is connected to the base unit 105, as shown in FIG. 5, then the controller 150 operates in the finger electrode mode (step 430). During the finger electrode mode (step 430), the base unit 105 shuts off or operates in a standby mode, and the controller 150 can maintain the display 175 on standby to conserve power in the power source 155 until the patient takes an action to initiate a data recording.

Figure 6:
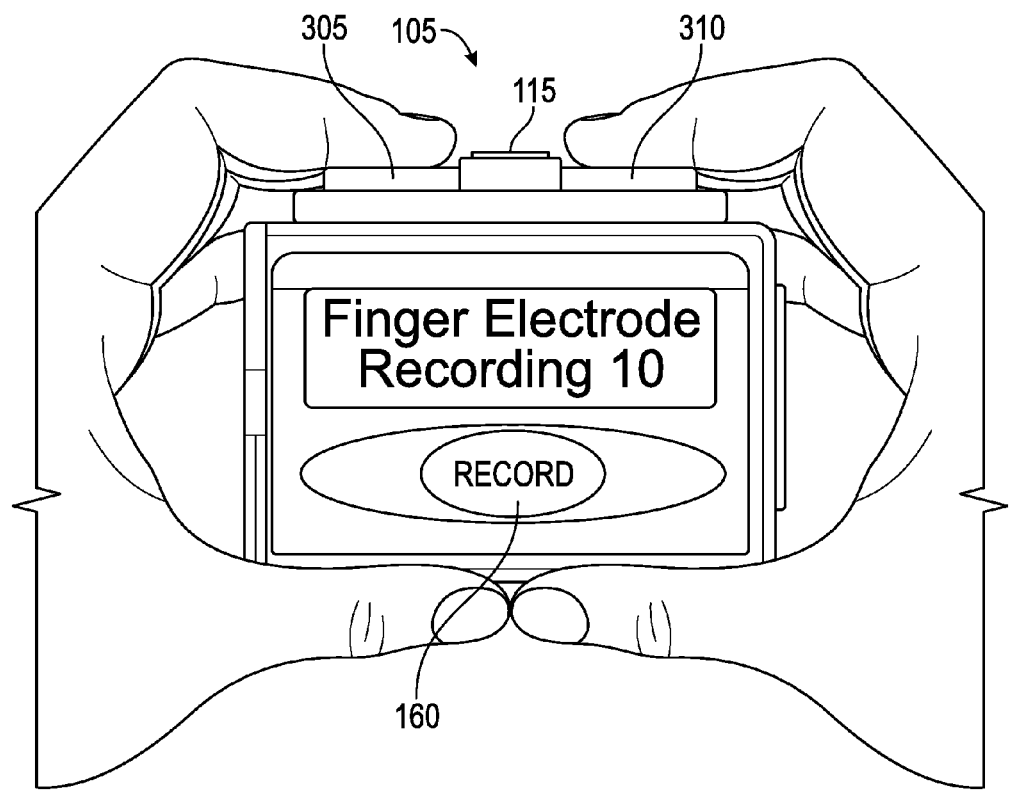
FIG. 6 is a perspective view showing a patient using the cardiac event monitoring system of FIG. 1 with the plug-in adapter of FIG. 3A connected to the base unit of FIGS. 2A and 2B.

When the patient experiences a symptom, he presses the symptom record button 160 and watches the display 175, as shown in FIG. 6. The controller 150 determines that the button 160 has been pressed and enters a countdown mode, sending signals to the display 175 to display a "countdown to record" message that instructs the patient to place the fingers on the electrodes 305, 310 such that the electrodes 305, 310 make contact with the fingers. After the controller 150 has completed counting down, the countdown mode ends, and the controller 150 causes the display 175 to display an indication that the base unit 105 is recording data. For example, the display 175 can display the message "Finger Electrode Recording XX", where XX is the number of seconds that were specified as a measurement duration during setup of the base unit 105. For example, as shown in FIG. 6, the display message is "Finger Electrode recording 10." The controller 150 counts down to zero from the XX value, and, upon reaching zero, the controller 150 enters a transmit prompt mode. The controller 150 can send a signal to the display 175 to display a message requesting that the patient transmit the recorded signal, as discussed below. The controller 150 operates in finger electrode mode (step 430) until it receives an indication that the plug-in adapter 115 is disconnected from the base unit 105 (step 425).

After the recording is complete, the patient disconnects either the wearable electrode system 110 or the plug-in adapter 115 from the base unit 105. Therefore, the controller 150 determines that the wearable electrode system 110 is not connected to the base unit 105 (step 405) and the plug-in adapter 115 is not connected to the base unit 105 (step 425). The controller 150 then determines if the yes/transmit button 165 has been pressed (step 435). In this implementation, the base unit 105 is configured to only transmit if both the wearable electrode system 110 and the plug-in adapter 115 are disconnected from the base unit 105. If the yes/transmit button 165 has not been pressed (step 435), then the controller 150 causes the base unit 105 to enter into standby mode to conserve energy (step 440).

If the controller 150 determines that the yes/transmit button 165 has been pressed (step 435), then the controller 150 operates in transmit mode (step 445). During transmit mode, the patient transmits the ECG data to a monitoring center using a telephone or some other suitable device. To transmit the ECG data, the patient calls the monitoring center, and follows the directions given by the monitoring center. Next, the patient places the base unit 105 on a flat surface near the telephone and places the mouthpiece of the phone behind the base unit 105. The patient presses the yes/transmit button 165, which indicates to the controller 150 to send a signal to the speaker 180 to start transmission of the ECG data. During transmission, the speaker 180 emits a series of tones that indicate the ECG data. If needed, in some circumstances, the patient can re-transmit ECG data.

The monitoring center staff reviews the tracings and, when necessary, notifies the patient's physician immediately. A report is generated and forwarded to the physician. In the implementation shown in FIG. 4, the patient removes the cable connector 135 of the wearable electrode system 110 and the plug-in adapter 115 from the base unit 105 prior to transmission.

Other implementations are within the scope of the following claims. For example, in other implementations, the base unit 105 could be configured to be able to transmit when either the wearable electrode system 110 or the plug-in adapter 115 is connected from the base unit 105. Thus, in this implementation, the patient is not required to remove the wearable electrode system 110 or the plug-in adapter 115 from the base unit 105 prior to transmitting the data. The patient may merely be required to press the transmit button 165 in order to initiate the transmit mode.

The base unit 105 can be any size suitable for permitting a patient to carry the base unit 105 on the patient's body without undue hardship.

Alternatively, the patient can wait to transmit the ECG data, which can be stored within the memory 152 of the controller 150, for a period of time after the data is recorded.

The plug-in adapter 115 can be formed from other suitable shapes, or can be ergonomically designed. For example, the adapter 115 can have a flat base that faces the base unit 105 when plugged into the base unit 105 and have a triangularly-shaped outer surface with two angled surfaces such that the electrodes 305, 310 are formed along the angled surfaces. As another example, the adapter 115 can have a flat base that faces the base unit 105 when plugged into the base unit 105 and have a concave or convex outer surface on which the electrodes 305, 310 are formed. The outer surface can be polygonal, with each side including an electrode. Although the plug-in adapter 115 is suitable for making contact between the patient's fingers and the electrodes 305, 310, the plug-in adapter 115, and, in particular, the electrodes 305, 310, can be contacted to any body part of the patient. For example, the electrodes 305, 310 can be contacted to the chest, the legs, or the arms of the patient. Moreover, the electrodes 305, 310 may be designed with different shapes or sizes.

The power source 155 may be turned off and on by a switch 205 (FIGS. 1 and 2B) accessible on the compartment 200 and connected to the power source 155 and the controller 150.

What is claimed is:

1. A cardiac event monitoring kit comprising:
   a base unit including a base connector;
   a wearable electrode system including a cable, an electrode at one end of the cable, and a cable connector at the other end of the cable, the cable connector being configured to plug into and be removed from the base connector; and
   a plug-in adapter comprising:
      a housing that includes at least two electrodes on an outer surface of the housing, wherein the at least two electrodes detect a signal from a patient's heart when one of the at least two electrodes is contacted by a finger of the patient's right hand while another of the at least two electrodes is simultaneously contacted by a finger of the patient's left hand, and
      an adapter connector formed on the housing, the adapter connector configured to plug into and to be removed from the base connector included in the base unit, and the adapter connector having an identifier that is configured to identify the plug-in adapter to the base unit when the plug-in adapter is connected to the base unit,
   wherein the base connector included in the base unit is configured to interchangeably receive the cable connector of the wearable electrode system or the adapter connector formed on the housing.

2. The cardiac event monitoring kit of claim 1 wherein the plug-in adapter comprises two electrodes.

3. The cardiac event monitoring kit of claim 1 wherein the electrodes of the plug-in adapter are each sized to receive a finger.

4. The cardiac event monitoring kit of claim 1 wherein the electrode of the wearable electrode system is configured to be attached to the patient's skin.

5. The cardiac event monitoring kit of claim 1 wherein the base unit comprises a controller that is configured to operate in an auto capture mode.

6. The cardiac event monitoring kit of claim 1 wherein the base unit comprises a speaker for transmitting data recorded from the plug-in adapter or the wearable electrode system.

7. The cardiac event monitoring kit of claim 1 wherein the base unit comprises memory for storing data recorded from the plug-in adapter or the wearable electrode system.

8. The cardiac event monitoring kit of claim 1 wherein the base unit comprises a display.

9. The cardiac event monitoring kit of claim 1 wherein the base unit comprises one or more input devices.

10. The cardiac event monitoring kit of claim 1 wherein the base unit comprises a controller that is configured to operate in a manual mode.

11. The system of claim 1, wherein the identifier is formed from a resistance that is internal to the adapter and has a resistance value that uniquely identifies the plug-in adapter.

12. A cardiac event monitoring kit comprising:
   a base unit including a base connector; and
   a plug-in adapter comprising:
      a housing including at least two electrodes on an outer surface of the housing, wherein the electrodes detect a signal from a patient's heart when one of the at least two electrodes is contacted by a finger of the patient's right hand while another of the at least two electrodes is simultaneously contacted by a finger of the patient's left hand, and
      an adapter connector formed on the housing, the adapter connector configured to plug into and to be removed from the base connector of the base unit, and an identifier that is configured to identify the plug-in adapter to the base unit when the plug-in adapter is connected to the base unit,
   wherein the base connector included in the base unit is configured to interchangeably receive a cable connector of a wearable electrode system or the adapter connector formed on the housing.

13. The cardiac event monitoring kit of claim 12 wherein the base unit comprises a controller that is configured to operate in an auto capture mode.

14. The cardiac event monitoring kit of claim 12 wherein each of the electrodes is sized to receive a finger.

15. The cardiac event monitoring kit of claim 12 wherein the base unit comprises a speaker for transmitting data recorded from the plug-in adapter or the wearable electrode system.

16. The cardiac event monitoring kit of claim 12 wherein the base unit comprises memory for storing data recorded from the plug-in adapter or the wearable electrode system.

17. A method of monitoring cardiac events, the method comprising:
   determining whether a wearable electrode system is connected to a base unit of a monitoring system, and if the wearable electrode system is connected to the base unit, operating the base unit to receive electrical signals from an electrode of the wearable electrode system;
   if the wearable electrode system is not connected to the base unit, determining whether a plug-in adapter is connected to the base unit using an identifier included in an adapter connector formed on a housing of the plug-in adapter; and
   if the plug-in adapter is connected to the base unit, operating the base unit to receive electrical signals from a patient's heart from at least two electrodes located on an outer surface of the housing of the plug-in adapter, one of the at least two electrodes being contacted by a finger of the patient's right hand and another of the at least two electrodes being simultaneously contacted by a finger of the patient's left hand.

18. The method of claim 17 further comprising transmitting the electrical signals to a monitoring center if it is determined that the patient requested that the electrical signals be transmitted.

19. The method of claim 17 wherein operating the base unit to receive electrical signals from the electrode of the wearable electrode system includes monitoring the patient's electrical signals and recording the electrical signals if it is determined that the electrical signals are abnormal.

20. The method of claim 17 further comprising storing in memory electrical signals received from the plug-in adapter or the wearable electrode system for a predetermined time or until the patient transmits the electrical signals.

21. The method of claim 17 further comprising displaying instructions to the patient on the base unit.

22. The method of claim 17 further comprising receiving instructions from the patient from one or more input devices on the base unit.

23. A method of monitoring cardiac events, the method comprising:
providing a plug-in adapter that includes at least two electrodes on an outer surface of a housing of the plug-in adapter, the electrodes being configured to detect a signal from a patient's heart when one of the at least two electrodes is contacted by a finger of the patient's right hand while another of the at least two electrodes is simultaneously contacted by a finger of the patient's left hand,
wherein the plug-in adapter comprises an adapter connector that is configured to plug into and to be removed from a base connector of a base unit, and an identifier that is included in an adapter connector formed on the housing of the plug-in adapter and configured to identify the plug-in adapter to the base unit when the plug-in adapter is connected to the base unit, and
wherein the base connector is configured to interchangeably receive the adapter connector or a cable connector of a wearable electrode system that includes a cable, an electrode at one end of the cable, and the cable connector at the other end of the cable.

24. A plug-in adapter comprising:
a housing;
two finger electrodes on an outer surface of one side of the housing, the two finger electrodes being positioned for contact with two fingers of a patient during use and the finger electrodes being configured to detect a signal from a patient's heart when each of the electrodes is contacted by a different finger of the patient; and
an adapter connector formed on another side of the housing;
wherein the adapter connector is configured to plug into a connector of a base unit of a cardiac event monitor, and the adapter connector includes an identifier to identify the plug-in adapter to the base unit when the plug-in adapter is connected to the base unit.

25. The system of claim 24, wherein one of the two finger electrodes is contacted by a finger of the patient's right hand while the other of the two finger electrodes is simultaneously contacted by a finger of the patient's left hand.

\* \* \* \* \*